United States Patent [19]
Bhatta

[11] Patent Number: 5,542,944
[45] Date of Patent: Aug. 6, 1996

[54] SURGICAL DEVICE AND METHOD

[76] Inventor: Krishan M. Bhatta, 60 High St., Skowhegan, Me. 04976

[21] Appl. No.: 311,728

[22] Filed: Sep. 23, 1994

Related U.S. Application Data

[63] Continuation of Ser. No. 49,136, Apr. 19, 1993, abandoned.
[51] Int. Cl.$^6$ ............................. A61B 17/36; A61B 1/00
[52] U.S. Cl. ............................................. 606/33; 606/16
[58] Field of Search .............................. 606/14, 15, 16, 606/17, 10, 39, 45, 33; 604/223

[56] References Cited

U.S. PATENT DOCUMENTS

| | | | |
|---|---|---|---|
| 3,413,976 | 12/1968 | Roze | 128/328 |
| 3,858,577 | 1/1975 | Bass et al. | 128/8 |
| 3,945,375 | 3/1976 | Banko | 604/22 |
| 4,027,674 | 6/1977 | Tessier et al. | 128/328 |
| 4,273,127 | 6/1981 | Auth et al. | 606/17 |
| 4,481,948 | 11/1984 | Sole | 606/45 |
| 4,784,132 | 11/1988 | Fox et al. | 606/15 |
| 4,887,600 | 12/1989 | Watson et al. | 606/128 |
| 4,932,954 | 6/1990 | Wondrazek et al. | 606/128 |
| 4,955,882 | 9/1990 | Hakky | 606/14 |
| 5,061,266 | 10/1991 | Hakky | 606/15 |
| 5,088,998 | 2/1992 | Sakashita et al. | 606/46 |
| 5,152,768 | 10/1992 | Bhatta | 606/128 |
| 5,285,795 | 2/1994 | Ryan et al. | 606/15 |
| 5,342,358 | 8/1994 | Daikuzono | 606/15 |
| 5,368,603 | 11/1994 | Halliburton | 606/17 |

FOREIGN PATENT DOCUMENTS

| | | | |
|---|---|---|---|
| 0189329 | 7/1986 | European Pat. Off. | 606/7 |
| 2747031 | 10/1977 | Germany | A61B 17/22 |
| 3840126 | 11/1988 | Germany | G10K 11/02 |
| 1531659 | 11/1978 | United Kingdom | A61B 17/22 |

OTHER PUBLICATIONS

American Urological Association, 1993 Annual Meeting, San Antonio, TX, Krishna M. Bhatta, presenter "Irrigating Electrode" (topic).

Lasers in Surgery and Medicine 11:481–483 (1991) By: Krishna Bhatta, Rattner, Haw and Nishioka Brief Report on "New Laser Delivery Device for Laparoscopic Procedures", accepted for publication Apr. 16, 1991.

The Journal of Urology, vol. 143, Apr., pp. 857–860 By: Bhatta et al., "Effects of Shielded or Unshielded Laser and Electrohydraulic Lithotripsy on Rabbit Bladder".

Richard Wolf Medical Instruments Corp., 7046 Lyndon Ave. Rosemont, IL 60018 Order catalog "Endourology Today" News and Trends Extracorporeal piezoelectric lithotripsy (12 pages).

Primary Examiner—Stephen C. Pellegrino
Assistant Examiner—Sonya C. Harris
Attorney, Agent, or Firm—Hayes, Soloway, Hennessey, Grossman & Hage, P.C.

[57] ABSTRACT

A surgical instrument adapted for use in prostate, intra-uterine, kidney, liver, bladder and urinary tract surgery and the like comprising an elongate flexible casing having a delivery tube for delivering a working fluid to the target tissue, and an optical fiber for delivering a coherent beam of electromagnetic radiation to the working fluid whereby to heat the working fluid and in turn thermally treat the target tissue.

15 Claims, 2 Drawing Sheets

SURGICAL DEVICE AND METHOD

This is a continuation of copending application Ser. No. 08/049,136 filed on Apr. 19, 1993, now abandoned.

FIELD OF THE INVENTION

Generally, the present invention relates to improved surgical devices and methods. The invention has particular utility for use in prostate, intra-uterine, bladder and urinary tract surgery, and will be described in connection with such utility, although other utilities are contemplated by the instant invention.

BACKGROUND OF THE INVENTION

In recent years, fiberoptic technology has revolutionized medical procedures. Nowhere have the advantages engendered by these advances been greater than in the area of surgical techniques. Due to their flexibility and relatively small size, surgical devices incorporating flexible light pipes (such as fiberoptics) may be inserted into bodily cavities through relatively small incisions, whereas prior to the advent of this technology, large incisions, and therefore major surgery was required for such access.

Fiberoptic surgical devices, once positioned within the bodily cavity, may be used to view body tissues contained within the cavity, and if properly adapted, to cut and remove undesired bodily tissue from the body cavity. It is often particularly useful for such fiberoptic cutting devices to use a coherent beam of electromagnetic radiation (e.g. a laser beam) to thermally damage undesired tissues. When struck by a low-power coherent beam, the undesired tissue may be cauterized and the tissue killed. Very often, one pulse of electromagnetic radiation may not be sufficient to destroy all of the undesired tissue. This may result in live, undesired tissue becoming covered by a layer of dead tissue. Disadvantageously, it may not be possible in such a situation, to destroy the underlying tissue without either increasing the strength of the coherent beam or providing some means for removing the dead tissues. Increasing the strength of the coherent beam may result in collateral damage to surrounding tissue. Additionally, the layer of dead tissues may prevent the surgeon from viewing the undesired underlying live tissue to be destroyed, and its presence thereby may go unnoticed.

Therefore, in light of the above problems, the prior art has proposed several fiberoptic surgical cutting tools capable of removing thermally damaged tissues. As will be presently seen, however, none of these devices are without serious drawbacks. For example, Hakky, U.S. Pat. No. 4,955,882, discloses a laser resectoscope with mechanical and laser cutting means for use in prostate surgery. The device disclosed by Hakky includes a rotating cutting element mounted within an outer sheath adapted to be inserted into the urethra. The cutting element contemplated by Hakky has helical threads along its length and a cutting blade at its distal end. Sheath means surround the cutting element except for the cutting blade. A fiberoptic laser filament for delivering laser energy to the issue site is positioned adjacent to the cutting blade. The laser filament is surrounded by a sheath and adapted to be moved by the rotation of the cutting element so that the laser beam emitted from the filament advances through the tissues to cut and coagulate the resected area before the cutting blade reaches them. Irrigation fluid is provided to the tissue site and ultrasound is used in conjunction with the laser resectoscope to plot the area of the prostate tissue to be removed. Computer control prevents cutting of tissue beyond the area of tissues desired to be removed.

Although providing somewhat effective means for removing undesired tissues after cauterization, Hakky's device is a single purpose surgical tool, i.e. for use in performing transurethrally prostate and/or bladder surgery. Also, Hakky's device, which employs a helical screw-type mechanical mechanism is complex, and thus relatively costly to manufacture and sterilize, and Hakky's device may be prone to mechanical breakdown. Moreover, while Hakky's device is designed to coagulate blood before bleeding occurs, some bleeding may still result, particularly from larger vessels, and thus obscure viewing, and provide a possible site for abscess formation.

Other patents showing the general nature of the state of the art in tissue cutting and removing devices are: U.S. Pat. No. 4,694,828 issued to Eichenbaum; U.S. Pat. No. 4,899,733 issued to DeCastro; and U.S. Pat. No. 5,590,200 issued to Tulip.

Approximately 400,000 prostate enlargements are treated surgically in the United States annually. The gold standard for this treatment is Transurethral Resection of Prostate (TURP) and is performed endoscopically using electrocautery loops. Bleeding is a problem following this procedure and the patient requires to be in the hospital with an indwelling catheter for 2–4 days. Frequently, continuous irrigation of the bladder is used to prevent clot retention in such cases. Recently, several alternative treatments have been developed in an attempt to manage these patients on lesser aggressive approaches including balloon dilatations, microwave heating of prostate tissue and pharmacological manipulations. These, however, do not remove the obstructing prostate tissue and lie short in a permanent treatment for BPH. More recently, laser has been used in an attempt to destroy the prostate tissue which then is passed by the patient over the next few weeks opening a channel for free urinary passage thus treating the bladder outlet obstruction thus caused by the enlarged prostate tissue. The drawback of this approach has been the fact that the patient has a suprapubic tube for bladder drainage for 10–14 days until he passes the dead and necrosed prostate tissue. Moreover, the dead tissue passed is no good for histological examination and thus chances of missing an occult prosatic carcinoma is always present.

SUMMARY OF THE INVENTION

The present invention also uses laser but uses it in conjunction with a mechanical support, irrigation and a cutting means (sharp or electrocautery) to be able to remove prostate tissue without bleeding in a similar way to TURP. The improved hemostasis is achieved by a combination of laser and irrigation. The irrigation cools the surface of the tissue irradiated by a laser which thus is allowed to penetrate deep into the tissue causing thermal cooking of the said tissue. The action is similar to boiling a potato rather than burning it over a flame. The laser along with mechanical support of the adjacent metal element which lies flush to the distal end of the device then working as a unit is able to cut the prostate tissue as desired. Finally, a loop with a sharp cutting element distally or an electrocautery element completes the procedure by cutting prostate into chips similar to TURP. Since there is no bleeding during this procedure, this procedure can possibly be performed under local anesthesia and without the need for an indwelling catheter following the surgery as a day case. Apart from major advantages to the patient this procedure may reduce the national cost of BPH treatment by reducing hospital costs and associated morbidity.

Accordingly, there is provided, in accordance with one aspect of the present invention, a surgical instrument adapted for insertion into a narrow or confined body cavity for use. The surgical instrument contemplated by the present invention comprises an elongate casing that has proximal and distal ends, and including means for delivering a coherent beam of electromagnetic radiation (i.e. laser energy) to the bodily tissues when the instrument is inserted into the bodily cavity and positioned nearby the body tissue, and means for delivering fluid from a fluid source to the body tissues. The coherent beam delivering means and the fluid delivering means which are contained within the casing each terminate in outlets at or adjacent to the distal end of the casing, whereby to permit delivery of a controlled stream or "shots" of fluid to selected body tissues to cool the surface of the tissue irradiated by the laser. This permits the use of a high powered laser to penetrate deep into the selected body tissues causing thermal cooking of the tissues which may then be removed, for example, by means of a mechanical blade.

BRIEF DESCRIPTION OF THE DRAWINGS

Other aspects, features, advantages, and utilities of the present invention will become apparent, as the following description proceeds, and upon reference to the hereinafter appended drawings wherein like numerals represent like parts, and wherein.

While the present invention will hereinafter be described in connection with a preferred embodiment and method of use, it will be understood that it is not intended to limit the invention to this embodiment or method of use. On the contrary, it is intended to cover all alternatives, modifications, and equivalents as may be included within the spirit and broad scope of the invention as defined by the hereinafter appended claims.

DESCRIPTION OF THE PREFERRED EMBODIMENT

Figure 1:
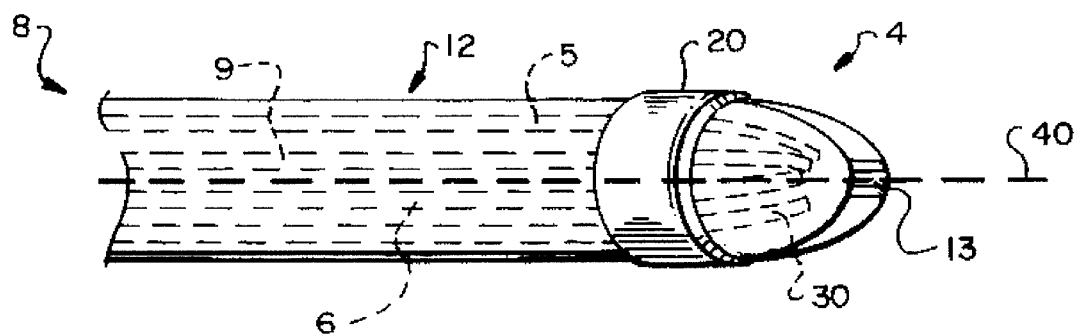
FIG. 1 depicts a top plan view of a preferred embodiment of the surgical device made in accordance with the present invention.

Turning to FIG. 1, a top plan view of a preferred form of surgical instrument made in accordance with and useful in accordance with the instant invention is depicted. The instrument comprises an elongate casing 12 having a proximal 8 and distal end 4. Conduit means 9 for directing fluid from a fluid source (not shown) is included within the casing 12 and terminates, together with a laser fiber 30, at or adjacent its proximal end 8, at an opening 13. The fluid thus directed through the fluid directing means may be used to irrigate the tissue site during surgery, thus cooling the tissue, and washing away debris whereby to permit the surgeon an unobstructed view of the tissue operating site via a standard cystoscope, or using a built in fiberoptic viewing means 5.

Figure 2:
FIG. 2 is a side view of the preferred embodiment depicted in FIG. 1.
Figure 3:
FIG. 3 is a view similar to FIG. 2 of an alternative embodiment shown of the surgical device made in accordance with the present invention.
Figure 6A:
FIGS. 6A, 6B and 6C show details of alternative shapes of a portion of the surgical device made in accordance with the present invention.
Figure 6B:
Figure 6C:

Referring also to FIG. 2, metal loop 20 is affixed adjacent the distal end 4 of casing 12 for "chipping" the "cooked" tissue. Loop 20 may be slanted backwards from distal end 4 as e.g. at an angle of 25° to 75° from the axis 40 of the casing 12, as shown in FIG. 2, or may be straight (90°) as shown in FIG. 3. Loop 20 may comprise a variety of shapes such as conical, cylindrical or quadrilateral, etc., as shown at 20A, 20B and 20C in FIGS. 6A, 6B and 6C, respectively.

Figure 5:
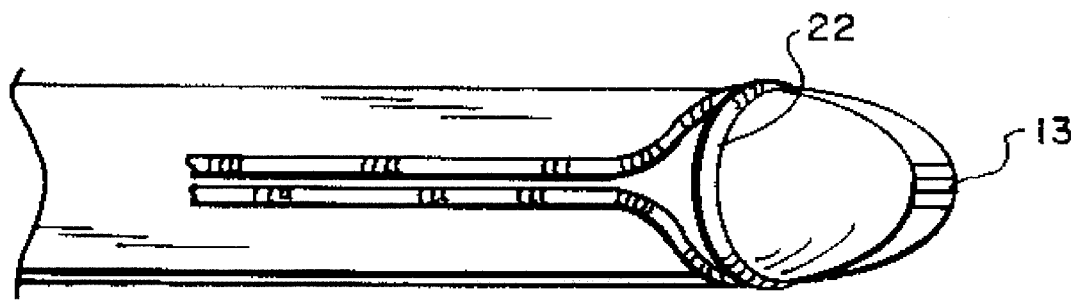
FIG. 5 is a top plan view showing yet another alternative embodiment of the surgical device made in accordance with present invention.

Alternatively, as illustrated in FIG. 5, an electrocautery loop 22 may be affixed adjacent the distal end 4 of casing 12 for "chipping" the "cooked" tissue. The instrument also includes means for illuminating the tissue area. Preferably, the illumination means takes the form of at least one optical fiber 6 contained within the casing 12 and operatively mounted (i.e. terminating) at or adjacent the distal end 4 of the casing 12. The illumination means floods the tissue site located nearby the distal end 4 of the instrument with light so that the surgeon may observe the tissue adjacent the distal end 4 of the surgical device as the operation progresses, using the telescope means 5. As will be appreciated by one skilled in the art, the telescope means 5 may take the form of a flexible optical fiber appropriately adapted for use as a viewing instrument. Fluid may be directed to the target tissue site to remove excess heat and debris by directing the fluid continuously, or sporadically, as needed.

A preferred method of using an instrument made according to the instant invention will now be described in connection with urinary tract surgery. First, the body 12 of the instrument is inserted into a body cavity, e.g. through the urethra. The instrument is then advanced within the urethra until its distal end 4 is positioned adjacent the target tissue to be treated. Once properly positioned, a controlled amount of fluid is delivered from the fluid directing means to the target tissue. Then radiation, which has a wavelength selected to not or minimally couple with the fluid, is delivered continuously or sporadically, as needed, by laser fiber 30 to "cook" the target tissue, thermally destroying the tissue and cauterizing any blood therein. The fluid thus cools the optical delivery fiber and the surface of the target tissue thus allowing high energies to be transmitted whereby to achieve deeper penetration of light energy into the tissue. The "cooked" tissue may than be removed, for example, by ablating the "cooked" tissue with the loop 20 or 22. Irrigating fluid is delivered, as needed, to cool the tissue. By directing cooling fluid onto the target tissue surface, the strength of the laser depth of penetration of subsequent laser shots may be increased thus improving hemostasis of the tissue, without damaging surrounding tissue.

Figure 4:
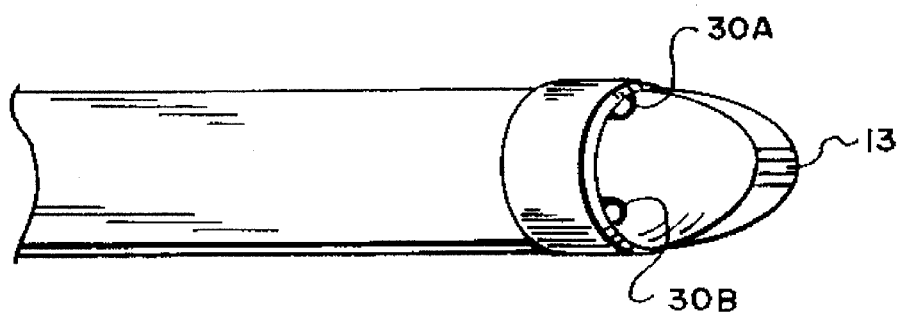
FIG. 4 is a top plan view of another alternative embodiment of the surgical device made in accordance with the present invention.

It is evident there has been provided, in accordance with the present invention, a surgical instrument and procedure for bloodless surgical treatment and removal of selected tissues. While this invention has been described in conjunction with a specific embodiment thereof, various alternatives and modifications may be made without departing from the spirit and scope of the invention. For example, as shown in FIG. 4, the laser fiber 30 may be divided into two fibers 30A, 30B adjacent the distal end 4 of the casing 12. Fibers 30A and 30B preferably are spaced to either side of the casing. Also, if desired, electrocautery loop 22 (FIG. 5) may be made detachable from the instrument. The invention advantageously may be used with a standard cystoscope and using video technology. Accordingly, it is intended to embrace all such alternatives, modifications, and variations that fall within the spirit and broad scope of the hereinafter appended claims.

What is claimed is:

1. A surgical instrument comprising in combination:
   a. an elongate casing having a proximal and distal end;
   b. means for delivering a fluid to target tissue, said fluid delivery means being carried within said casing and terminating adjacent the distal end of said casing;
   c. means for delivering a coherent beam of electromagnetic radiation to said fluid whereby to heat said target tissue, said delivery means being carried within said casing and terminating adjacent said distal end thereof; and
   d. a stationary cutting blade affixed to the outer surface of said casing adjacent to and spaced rearwardly from said distal end for aiding in removal of said target tissue.

2. An instrument according to claim 1, further comprising optical fiber means carried within said casing and terminating adjacent the distal end of said casing for illuminating areas adjacent the distal end of said casing.

3. An instrument according to claim 1, further comprising optical viewing means carried within said casing and terminating adjacent the distal end of said casing.

4. An instrument according to claim 1, and including an electrocautery loop affixed adjacent the distal end of said casing.

5. An instrument according to claim 4, wherein said electrocautery loop is detachable.

6. An instrument according to claim 1, wherein said casing comprises a major axis, and said blade includes cutting edges that form an approximately 90° angle with the axis of said casing.

7. An instrument according to claim 6, wherein said blade includes cutting edges on both proximal and distal edges thereof.

8. An instrument according to claim 6, wherein said blade is generally cone shaped.

9. An instrument according to claim 6, wherein said blade is generally cylindrically shaped.

10. An instrument according to claim 6, wherein said blade is generally quadrangularly shaped.

11. An instrument according to claim 1, wherein said casing comprises a major axis, and said blade includes cutting edges that form an angle in the range of 25° to 75° from the axis of said casing.

12. In a method of treating target tissue within a body using a device according to claim 1, said method including delivering electromagnetic radiation to the target tissue by said beam delivery means, the improvement which comprises, substantially simultaneously, cooling the electromagnetic energy and the target tissue by means of said fluid, and removing said target tissue using said blade.

13. A method according to claim 12 for use in prostate, intra-uterine, bladder and urinary tract surgery.

14. A surgical instrument, and comprising:
   a. an elongate casing having a proximal and distal end;
   b. means for delivering a fluid to target tissue, said fluid delivery means being carried within said casing and terminating adjacent the distal end of said casing;
   c. means for delivering a coherent beam of electromagnetic radiation to said fluid whereby to heat said target tissue, said delivery means being carried within said casing and terminating adjacent said distal end thereof; and
   d. a stationary cutting blade affixed to the outer surface of said casing adjacent to and spaced rearwardly from said distal end for aiding in removal of said target tissue, said blade being adapted to be energized so as to provide an electrocautery element.

15. In a method according to claim 12, wherein said target tissue comprises prostate, intra-uterine, bladder, and urinary tract tissue.

* * * * *